(12) United States Patent
Marshall et al.

(10) Patent No.: US 8,366,689 B2
(45) Date of Patent: Feb. 5, 2013

(54) METHOD FOR MAKING STRUCTURAL CHANGES IN CORNEAL FIBRILS

(75) Inventors: John Marshall, Farnborough (GB); Ali Hussein, Waltham, MA (US); David Muller, Boston, MA (US)

(73) Assignee: Avedro, Inc., Waltham, MA (US)

( * ) Notice: Subject to any disclaimer, the term of this patent is extended or adjusted under 35 U.S.C. 154(b) by 459 days.

(21) Appl. No.: 12/570,959

(22) Filed: Sep. 30, 2009

(65) Prior Publication Data

US 2010/0094197 A1 Apr. 15, 2010

Related U.S. Application Data

(60) Provisional application No. 61/101,496, filed on Sep. 30, 2008.

(51) Int. Cl.
*A61M 35/00* (2006.01)
*A61B 18/18* (2006.01)
(52) U.S. Cl. ............... 604/290; 604/294; 606/5
(58) Field of Classification Search ............ 604/20, 604/289, 294, 290; 606/4, 5
See application file for complete search history.

(56) References Cited

U.S. PATENT DOCUMENTS

| | | | |
|---|---|---|---|
| 4,326,529 A | 4/1982 | Doss et al. |
| 4,381,007 A | 4/1983 | Doss |
| 4,712,543 A | 12/1987 | Baron |
| 4,764,007 A | 8/1988 | Task |
| 4,805,616 A | 2/1989 | Pao |
| 4,881,543 A | 11/1989 | Trembly et al. |
| 4,891,043 A | 1/1990 | Zeimer et al. |
| 4,994,058 A | 2/1991 | Raven et al. |
| 5,016,615 A | 5/1991 | Driller et al. |
| 5,103,005 A | 4/1992 | Gyure et al. |
| 5,171,254 A | 12/1992 | Sher |
| 5,281,211 A | 1/1994 | Parel et al. |
| 5,332,802 A | 7/1994 | Kelman et al. |
| 5,461,212 A | 10/1995 | Seiler et al. |

(Continued)

FOREIGN PATENT DOCUMENTS

| | | |
|---|---|---|
| EP | 1 561 440 A1 | 8/2005 |
| EP | 1 790 383 A1 | 5/2007 |

(Continued)

OTHER PUBLICATIONS

Chandonnet, CO2 Laser Annular Thermokeratoplasty: A Preliminary Study, Lasers in Surgery and Medicine 12:264-273 (1992), Wiley-Lill, Inc.

(Continued)

*Primary Examiner* — Kevin C Sirmons
*Assistant Examiner* — Bradley Osinski
(74) *Attorney, Agent, or Firm* — Nixon Peabody LLP

(57) ABSTRACT

In a system for stabilizing a pattern of structural changes in corneal fibrils, an eye treatment system causes corneal fibrils of a cornea of an eye to transition from a first structure to a second structure. An application device applies a cross-linking element to the corneal fibrils. An activating device applies an initiating element to the corneal fibrils and activates the cross-linking element. The cross-linking element causes cross-linking in the corneal fibrils to preserve the second structure of the corneal fibrils. Another application device may apply a cross-linking breaker to the corneal fibrils. The cross-linking breaker halts or reverses at least partially the cross-linking in the corneal fibrils. Another activating device applies an initiating element to the corneal fibrils and activates the cross-linking breaker. Advantageously, the cross-linking breaker provides greater control over the amount and progress of cross-linking that occurs in the corneal fibrils.

25 Claims, 11 Drawing Sheets

U.S. PATENT DOCUMENTS

| | | | |
|---|---|---|---|
| 5,490,849 A | 2/1996 | Smith |
| 5,512,966 A | 4/1996 | Snook |
| 5,618,284 A | 4/1997 | Sand |
| 5,634,921 A | 6/1997 | Hood et al. |
| 5,766,171 A | 6/1998 | Silvestrini |
| 5,779,696 A | 7/1998 | Berry et al. |
| 5,814,040 A | 9/1998 | Nelson et al. |
| 5,885,275 A | 3/1999 | Muller |
| 5,891,131 A | 4/1999 | Rajan et al. |
| 5,910,110 A | 6/1999 | Bastable |
| 6,033,396 A | 3/2000 | Huang et al. |
| 6,101,411 A | 8/2000 | Newsome |
| 6,104,959 A | 8/2000 | Spertell |
| 6,139,876 A | 10/2000 | Kolta |
| 6,161,544 A | 12/2000 | DeVore et al. |
| 6,162,210 A | 12/2000 | Shadduck |
| 6,293,938 B1 | 9/2001 | Muller |
| 6,319,273 B1 | 11/2001 | Chen et al. |
| 6,325,792 B1 | 12/2001 | Swinger et al. |
| 6,334,074 B1 | 12/2001 | Spertell |
| 6,342,053 B1 | 1/2002 | Berry |
| 6,402,739 B1 | 6/2002 | Neev |
| 6,413,255 B1 | 7/2002 | Stern |
| 6,478,792 B1 | 11/2002 | Hansel |
| 6,520,956 B1 | 2/2003 | Huang |
| 6,520,958 B1 | 2/2003 | Shimmick et al. |
| 6,537,545 B1 * | 3/2003 | Karageozian et al. ........ 424/94.4 |
| 6,572,849 B2 | 6/2003 | Shahinian, Jr. |
| 6,617,963 B1 | 9/2003 | Watters et al. |
| 6,918,904 B1 | 7/2005 | Peyman |
| 6,946,440 B1 | 9/2005 | DeWoolfson |
| 7,044,945 B2 | 5/2006 | Sand |
| 7,073,510 B2 | 7/2006 | Redmond et al. |
| 7,130,835 B2 | 10/2006 | Cox et al. |
| 7,141,049 B2 | 11/2006 | Stern et al. |
| 7,192,429 B2 | 3/2007 | Trembly |
| 7,270,658 B2 | 9/2007 | Woloszko et al. |
| 7,331,350 B2 | 2/2008 | Kochevar et al. |
| 7,402,562 B2 | 7/2008 | DeWoolfson |
| 2002/0002369 A1 | 1/2002 | Hood |
| 2002/0013577 A1 | 1/2002 | Frey et al. |
| 2002/0049437 A1 | 4/2002 | Silvestrini |
| 2002/0099363 A1 | 7/2002 | Woodward et al. |
| 2002/0164379 A1 | 11/2002 | Nishihara et al. |
| 2003/0018255 A1 | 1/2003 | Martin et al. |
| 2003/0175259 A1 | 9/2003 | Karageozian et al. |
| 2003/0216728 A1 | 11/2003 | Stern et al. |
| 2004/0001821 A1 | 1/2004 | Silver et al. |
| 2004/0071778 A1 | 4/2004 | Bellmann et al. |
| 2004/0111086 A1 | 6/2004 | Trembly |
| 2004/0143250 A1 | 7/2004 | Trembly |
| 2004/0199158 A1 | 10/2004 | Hood et al. |
| 2004/0204707 A1 * | 10/2004 | Hood et al. ............... 606/41 |
| 2004/0243160 A1 | 12/2004 | Shiuey et al. |
| 2005/0038471 A1 | 2/2005 | Chan et al. |
| 2005/0149006 A1 | 7/2005 | Peyman |
| 2005/0271590 A1 | 12/2005 | Schwartz et al. |
| 2006/0135957 A1 | 6/2006 | Panescu |
| 2006/0149343 A1 | 7/2006 | Altshuler et al. |
| 2006/0177430 A1 * | 8/2006 | Bhushan et al. ............ 424/94.1 |
| 2006/0189964 A1 | 8/2006 | Anderson et al. |
| 2006/0276777 A1 | 12/2006 | Coroneo |
| 2006/0287662 A1 | 12/2006 | Berry et al. |
| 2007/0048340 A1 | 3/2007 | Bran et al. |
| 2007/0055227 A1 | 3/2007 | Khalaj et al. |
| 2007/0074722 A1 | 4/2007 | Giroux et al. |
| 2007/0099966 A1 * | 5/2007 | Fabricant ................. 514/350 |
| 2007/0123845 A1 | 5/2007 | Lubatschowski |
| 2007/0135805 A1 | 6/2007 | Peyman |
| 2007/0142828 A1 | 6/2007 | Peyman |
| 2007/0161976 A1 | 7/2007 | Trembly |
| 2007/0203547 A1 | 8/2007 | Costello et al. |
| 2007/0244470 A1 | 10/2007 | Barker et al. |
| 2007/0244496 A1 | 10/2007 | Hellenkamp |
| 2007/0265603 A1 | 11/2007 | Pinelli |
| 2008/0009901 A1 | 1/2008 | Redmond et al. |
| 2008/0015660 A1 | 1/2008 | Herekar |
| 2008/0027328 A1 | 1/2008 | Klopotek et al. |
| 2008/0114283 A1 | 5/2008 | Mattson et al. |
| 2008/0139671 A1 | 6/2008 | Herekar |
| 2008/0208177 A1 | 8/2008 | Mrochen et al. |
| 2009/0024117 A1 | 1/2009 | Muller |
| 2009/0054879 A1 | 2/2009 | Berry |
| 2009/0069798 A1 | 3/2009 | Muller et al. |
| 2009/0149842 A1 | 6/2009 | Muller et al. |
| 2009/0149923 A1 | 6/2009 | Herekar |
| 2009/0171305 A1 | 7/2009 | El Hage |
| 2009/0192437 A1 | 7/2009 | Soltz et al. |
| 2009/0209954 A1 | 8/2009 | Muller et al. |
| 2009/0275929 A1 | 11/2009 | Zickler |
| 2009/0276042 A1 | 11/2009 | Hughes et al. |
| 2010/0028407 A1 | 2/2010 | Del Priore et al. |
| 2010/0036488 A1 | 2/2010 | De Juan, Jr. et al. |
| 2010/0057060 A1 | 3/2010 | Herekar |
| 2010/0069894 A1 | 3/2010 | Mrochen et al. |
| 2010/0114109 A1 | 5/2010 | Peyman |
| 2010/0149842 A1 | 6/2010 | Muller et al. |
| 2010/0173019 A1 | 7/2010 | Paik et al. |
| 2010/0189817 A1 | 7/2010 | Krueger et al. |
| 2010/0210996 A1 | 8/2010 | Peyman |
| 2010/0286156 A1 | 11/2010 | Pinelli |
| 2010/0318017 A1 | 12/2010 | Lewis et al. |
| 2011/0077624 A1 | 3/2011 | Brady et al. |
| 2011/0098790 A1 | 4/2011 | Daxer |
| 2011/0118654 A1 | 5/2011 | Muller et al. |
| 2011/0152219 A1 | 6/2011 | Stagni et al. |
| 2011/0190742 A1 | 8/2011 | Anisimov |
| 2011/0208300 A1 | 8/2011 | Eugene et al. |

FOREIGN PATENT DOCUMENTS

| | | | |
|---|---|---|---|
| EP | 2 253 321 A1 | 11/2010 |
| IT | MI2010A001236 | 5/2010 |
| WO | 0074648 A2 | 12/2000 |
| WO | WO 2004/052223 A2 | 6/2004 |
| WO | WO 2005/110397 A1 | 11/2005 |
| WO | WO 2006/012947 A2 | 2/2006 |
| WO | 2006128038 A2 | 11/2006 |
| WO | WO 2007/001926 A2 | 1/2007 |
| WO | 2007/120457 A2 | 10/2007 |
| WO | WO 2008/000478 A1 | 1/2008 |
| WO | WO 2010/011119 A1 | 1/2010 |
| WO | WO 2010/023705 A1 | 3/2010 |

OTHER PUBLICATIONS

Muller et al., Br. J. Opthalmol 2001; 85:437-443 (April).

Naoumidi et al., J. Cataract Refract Surg. May 2006; 32(5):732-41.

Pallikaris et al., J. Cataract Refract Surg. Aug. 2005; 31(8):1520-29.

Acosta et al., Cornea. Aug. 2006;25(7):830-8.

Baier J. et al., "Singlet Oxygen Generation by UVA Light Exposure of Endogenous Photosensitizers," *Biophysical Journal*, vol. 91(4), pp. 1452-1459; Aug. 15, 2006 (8 pages).

Chan B.P., et al., "Effects of photochemical crosslinking on the microstructure of collagen and a feasibility study on controlled protein release;" *Acta Biomaterialia*, vol. 4, Issue 6, pp. 1627-1636; Jul. 1, 2008 (10 pages).

Clinical Trials.gov, "Riboflavin Mediated Corneal Crosslinking for Stabilizing Progression of Keratoconus (CCL)," University Hospital Freiburg, Feb. 20, 2008; retrieved from http://www.clinicaltrials.gov/ct2/show/NCT00626717, on Apr. 26, 2011 (3 pages).

Corbett M., et al., "Effect of Collagenase Inhibitors on Corneal Haze after PRK," *Exp. Eye Res.*, vol. 72, Issue 3, pp. 253-259; Jan. 2001 (7 pages).

Coskenseven E. et al., "Comparative Study of Corneal Collagen Cross-linking With Riboflaving and UVA Irradiation in Patients With Keratoconus," *Journal of Refractive Surgery*, vol. 25, issue 4, pp. 371-376; Apr. 2009 (6 pages).

"Definity (perflutren) injection, suspension [Bristol-Myers Squibb Medical Imaging]," http://dailymed.nlm.nih.gov/dailymed/drugInfo.cfm?id=8338, revised Sep. 2008, retrieved via the internet archive from http://web.archive.org/web/20100321105500/http://dailymed.nlm.nih.gov/dailymed/drugInfo.cfm?id=8338, on Dec. 14, 2011 (15 pages).

Ehlers W., et al., "Factors Affecting Therapeutic Concentration of Topical Aminocaproic Acid in Traumatic Hyphema," *Investigative*

*Ophthalmology & Visual Science*, vol. 31, No. 11, pp. 2389-2394; Nov. 1990 (6 pages).

Erskine H., "Avedro Becomes Sponsor of US FDA Clinical Trials of Corneal Collagen Crosslinking," Press Release, Mar. 16, 2010 (1 page).

Glenn J.V., et al., "Advanced Glycation End Product (AGE) Accumulation on Bruch's Membrane: Links to Age-Related RPE Dysfunction;" *Investigative Ophthalmology & Visual Science*, vol. 50, No. 1, pp. 441-451; Jan. 2009 (11 pages).

Gravitz L., "Laser Show in the Surgical Suite: Lasers and a century-old dye could supplant needles and thread;" *technology review*, MIT, Mar./Apr. 2009; retrieved from http://www.technologyreview.com/biomedicine/22088/?nlid=1767, on Sep. 26, 2011 (2 pages).

Hafezi F., et al., "Collagen Crosslinking with Ultraviolet-A and Hypoosmolar Riboflavin Solution in Thin Corneas," *J. Catract Refract. Surg.*, vol. 35, No. 1, pp. 621-624; Apr. 2009 (4 pages).

How to Use Definity: "Frequently Asked Questions;" retrieved from http://www.definityimaging.com/how-faq.html, on Sep. 26, 2011 (3 pages) (date unknown, prior to Apr. 26, 2010).

Imex, "KXL System: Crosslinking Para Cirugia Corneal Bibliografia Cientifica," Product Literature, Nov. 23, 2010 (24 pages).

Kampik D. et al., "Influence of Corneal Collagen Crosslinking With Riboflavin and Ultraviolet-A Irradiation on Excimer Laser Surgery," *Investigative Opthalmology & Visual Science*, vol. 51, No. 8, pp. 3929-3934; Aug. 2010 (6 pages).

Kissner Anja, et al., "Pharmacological Modification of the Epithelial Permeability by Benzalkonium Chloride in UVA/Riboflavin Corneal Collagen Cross-Linking," *Current Eye Research* 35(8), pp. 715-721; Mar. 2010 (7 pages).

Koller T., et al., "Therapeutische Quervernetzung der Hornhaut mittels UVA und Riboflavin: Therapeutic Cross-Linking of the Cornea Using Riboflavin/UVA," *Klinische Monatsblätter für Augenheilkunde*, vol. 224, No. 9, pp. 700-706; Sep. 2007 (7 pages).

Krueger, Ronald R., "Rapid VS Standard Collagen CXL with Equivalent Energy Dosing," presentation slides, (26 pages); available at http://www.slideshare.net/logen/krueger-herekar-rapid-cross-linking (date unknown, prior to Nov. 9, 2009).

Mi S., et al., "The adhesion of LASIK-like flaps in the cornea: effects of cross-linking, stromal fibroblasts and cytokine treatment," presented at British Society for Matrix Biology annual Meeting, Cardiff, UK, Sep. 8-9, 2008 (17 pages).

Mulroy L., et al., "Photochemical Keratodesmos for repair of Lamellar corneal Incisions;" *Investigative Ophthalmology & Visual Science*, vol. 41, No. 11, pp. 3335-3340; Oct. 2000 (6 pages).

O'Neil A.C., et al., "Microvascular Anastomosis Using a Photochemical Tissue Bonding Technique;" *Lasers in Surgery and Medicine*, vol. 39, Issue 9, pp. 716-722; Oct. 2007 (7 pages).

Paddock C., Medical News Today: "Metastatic Melanoma PV-10 Trial Results Encouraging Says Drug Company;" Jun. 9, 2009; retrieved from http://www.medicalnewstoday.com/articles/153024.php, on Sep. 26, 2011 (2 pages).

Pinelli R., et al., "C3-Riboflaving Treatments: Where Did We Come From? Where Are We Now?" *Cataract & Refractive Surgery Today Europe*, Summer 2007, pp. 36-46; Jun. 2007 (10 pages).

Ponce C., et al., "Central and Peripheral Corneal Thickness Measured with Optical Coherence Tomography, Scheimpflug Imaging, and Ultrasound Pachymetry in Normal, Keratoconus-suspect and Post-laser in situ Keratomileusis Eyes," *J. Cataract Refract. Surgery*, vol. 35, No. 6, pp. 1055-1062; Jun. 2009 (8 pages).

Proano C.E., et al., "Photochemical Keratodesmos for Bonding Corneal Incisions;" *Investigative Ophthalmology & Visual Science*, vol. 45, No. 7, pp. 2177-2181; Jul. 2004 (5 pages).

Rocha K., et al., "Comparative Study of Riboflavin-UVA Crosslinking and "Flash-linking" Using Surface Wave Elastometry," *Journal of Refractive Surgery*, vol. 24 Issue 7, pp. S748-S751; Sep. 2008 (4 pages).

RxList: "Definity Drug Description;" *The Internet Drug Index*, revised Jun. 16, 2008, retrieved from http://www.rxlist.com/definity-drug.htm, on Sep. 26, 2011 (4 pages).

Sheehan M., et al., "Illumination System for Corneal Collagen Crosslinking," *Optometry and Vision Science*, vol. 88, No. 4, pp. 512-524; Apr. 2011 (13 pages).

Shell, J., "Pharmacokinetics of Topically Applied Ophthalmic Drugs," *Survey of Ophthalmology*, vol. 26, No. 4, pp. 207-218; Jan.-Feb. 1982 (12 pages).

Sonoda S., "Gene Transfer to Corneal Epithelium and Keratocytes Mediated by Ultrasound with Microbubbles," *Investigative Ophthalmology & Visual Science*, vol. 47, No. 2, pp. 558-564; Feb. 2006 (7 pages).

Spoerl E., et al., "Artificial Stiffening of the Cornea by Induction of Intrastromal Cross-links," *Der Ophthalmologe*, vol. 94, No. 12, pp. 902-906; Dec. 1997 (5 pages).

Spoerl E., et al., "Induction of Cross-links in Corneal Tissue," *Experimental Eye Research*, vol. 66, Issue 1, pp. 97-103; Jan. 1998 (7 pages).

Spoerl E., et al., "Techniques for Stiffening the Cornea," *Journal of Refractive Surgery*, vol. 15, Issue 6, pp. 711-713; Nov.-Dec. 1999 (4 pages).

Spoerl E. et al., "Safety of UVA-Riboflavin Cross-Linking of the Cornea," *Cornea*, vol. 26, No. 4, pp. 385-389; May 2007 (5 pages).

Tessier FJ, et al., "Rigidification of Corneas Treated in vitro with Glyceraldehyde: Characterization of Two Novel Crosslinks and Two Chromophores," Investigative Opthalmology & Visual Science, vol. 43, E-Abstract; 2002 (2 pages).

"UV-X: Radiation System for Treatment of Keratokonus," *PESCHKE Meditrade GmbH*; retrieved from http://www.peschkemed.ch/ on Sep. 27, 2011 (1 page) (date unknown, prior to Sep. 16, 2008).

Vasan S., et al., "An agent cleaving glucose-derived protein crosslinks in vitro and in vivo;" *Letters to Nature*, vol. 382, pp. 275-278; Jul. 18, 1996 (4 pages).

Wollensak G., et al., "Collagen Crosslinking of Human and Porcine Sclera," *J. Cataract Refract. Surg.*, vol. 30, Issue 3, pp. 689-695; Mar. 2004 (7 pages).

Wollensak G., et al., "Riboflavin/Ultraviolet-A-induced Collagen Crosslinking for the Treatment of Keratoconus," *American Journal of Ophthalmology*, vol. 135, No. 5, pp. 620-627; May 2003 (8 pages).

Wollensak G., et al., "Cross-linking of Scleral Collagen in the Rabbit Using Riboflavin and UVA," *Acta Ophtalmologica Scandinavica*, vol. 83(4), pp. 477-482; Aug. 2005 (6 pages).

Wollensak G., "Crosslinking Treatment of Progressive Keratoconus: New Hope," *Current Opinion in Ophthalmology*, vol. 17(4), pp. 356-360; Aug. 2006 (5 pages).

Wollensak G., et al., "Hydration Behavior of Porcine Cornea Crosslinked with Riboflavin and Ultraviolet," A.J. Cataract Refract. Surg., vol. 33, Issue 3, pp. 516-521; Mar. 2007 (6 pages).

Wollensak G., et al., "Biomechanical and Histological Changes After Corneal Crosslinking With and Without Epithelial Debridement," *J. Cataract Refract. Surg.*, vol. 35, Issue 3, pp. 540-546; Mar. 2009 (7 pages).

Yang H., et al., "3-D Histomorphometry of the Normal and Early Glaucomatous Monkey Optic Nerve Head: Lamina Cribrosa and Peripapillary Scleral Position and Thickness," *Investigative Ophthalmology & Visual Science*, vol. 48, No. 10, pp. 4597-4607; Oct. 2007 (11 pages).

Zderic V., et al., "Drug Delivery Into the Eye With the Use of Ultrasound," *J. Ultrasound Med*, vol. 23(10), pp. 1349-1359; Oct. 2004 (11 pages).

Zderic V., et al., "Ultrasound-enhanced Transcorneal Drug Delivery," *Cornea* vol. 23, No. 8, pp. 804-811; Nov. 2004 (8 pages).

International Preliminary Report on Patentability, Search Report, and Written Opinion of the International Searching Authority for International Application No. PCT/US2009/059061, mailed Apr. 5, 2011 (7 pages).

International Search Report for PCT/US2010/029806 dated Jun. 1, 2010 (3 pages).

Written Opinion for PCT/US2010/029806 dated Jun. 1, 2010 (6 pages).

International Search Report for PCT/US2010/029791 dated Jun. 1, 2010 (3 pages).

Written Opinion for PCT/US2010/029791 dated Jun. 1, 2010 (6 pages).

Trembly et al.; Microwave Thermal Keratoplasty for Myopia: Keratoscopic Evaluation in Procine Eyes; Journal of Refractive Surgery; vol. 17; Nov./Dec. 2001; (8 pages).

Berjano et al; "Radio-Fequeny Heating of the Cornea: Theoretical Model and In Vito Experiments"; IEEE Transactions on Biomedical Engineering; vol. 49; No. 3; Mar. 2002; pp. 196-205.

Berjano et. al.; "Ring Electrode For Radio-Frequency Heating of the Cornea: Modeling And In Vitro Experiments"; Medical & Biological Engineering & Computing 2003; vol. 41; pp. 630-639.

International Search Report mailed Aug. 14, 2009 for PCT/US2009/042204, (5 pages).

International Search Report mailed Nov. 20, 2009 for PCT/2009/059061 (3 pages).

International Search Report mailed Nov. 6, 2009 for PCT/US2009/057481 (2 pages).

\* cited by examiner

METHOD FOR MAKING STRUCTURAL CHANGES IN CORNEAL FIBRILS

CROSS REFERENCE TO RELATED APPLICATIONS

This application claims priority to U.S. Provisional Application No. 61/101,496, filed Sep. 30, 2008, the contents of which are incorporated entirely herein by reference.

BACKGROUND OF THE INVENTION

1. Field of the Invention

The invention pertains to the field of keratoplasty and, more particularly, to systems and methods for stabilizing changes to treated corneal tissue.

2. Description of Related Art

A variety of eye disorders, such as myopia, keratoconus, and hyperopia, involve abnormal shaping of the cornea. Keratoplasty reshapes the cornea to correct such disorders. For example, with myopia, the shape of the cornea causes the refractive power of an eye to be too great and images to be focused in front of the retina. Flattening aspects of the cornea's shape through keratoplasty decreases the refractive power of an eye with myopia and causes the image to be properly focused at the retina.

Invasive surgical procedures, such as laser-assisted in-situ keratomileusis (LASIK), may be employed to reshape the cornea. However, such surgical procedures may typically require an extended healing period after surgery. Furthermore, such surgical procedures may involve complications, such as dry eye syndrome caused by the severing of corneal nerves.

Thermokeratoplasty, on the other hand, is a noninvasive procedure that may be used to correct the vision of persons who have disorders associated with abnormal shaping of the cornea, such as myopia, keratoconus, and hyperopia. Thermokeratoplasty may be performed by applying electrical energy in the microwave or radio frequency (RF) band. In particular, microwave thermokeratoplasty may employ a near field microwave applicator to apply energy to the cornea and raise the corneal temperature. At about 60° C., the collagen fibers in the cornea shrink. The onset of shrinkage is rapid, and stresses resulting from this shrinkage reshape the corneal surface. Thus, application of heat energy according to particular patterns, including, but not limited to, circular or annular patterns, may cause aspects of the cornea to flatten and improve vision in the eye.

SUMMARY OF THE INVENTION

Embodiments according to aspects of the present invention provide systems and methods for stabilizing corneal tissue and improving biomechanical strength after desired structural changes have been achieved in the corneal tissue. For example, the embodiments help to preserve the desired reshaping of the cornea produced by the application of thermokeratoplasty.

Accordingly, in an embodiment for stabilizing a pattern of structural changes in corneal fibrils, an eye treatment system causes corneal fibrils of a cornea of an eye to transition from a first structure to a second structure. An application device applies an advanced glycation endproduct (AGE) forming agent to the corneal fibrils. An activating device applies an initiating element to the corneal fibrils and activates the AGE forming agent. The AGE forming agent causes cross-linking in the corneal fibrils to preserve the second structure of the corneal fibrils. The AGE forming agent may be glycolaldehyde (GA).

Correspondingly, in an embodiment for changing a pattern of structural changes in corneal fibrils of a cornea of an eye, the structural changes include cross-linking of the corneal fibrils. An application device applies a cross-linking breaker to the corneal fibrils. An activating device applies an initiating element to the corneal fibrils and activates the cross-linking breaker. The cross-linking breaker halts or reverses at least partially the cross-linking in the corneal fibrils. In some embodiments, the cross-linking is caused by an advanced glycation endproduct (AGE) forming agent, such as glycolaldehyde (GA), and the cross-linking breaker may be an analog of phenacylthiazolium bromide (PTB), such as alagebrium.

These and other aspects of the present invention will become more apparent from the following detailed description of the preferred embodiments of the present invention when viewed in conjunction with the accompanying drawings.

DETAILED DESCRIPTION

Figure 1:
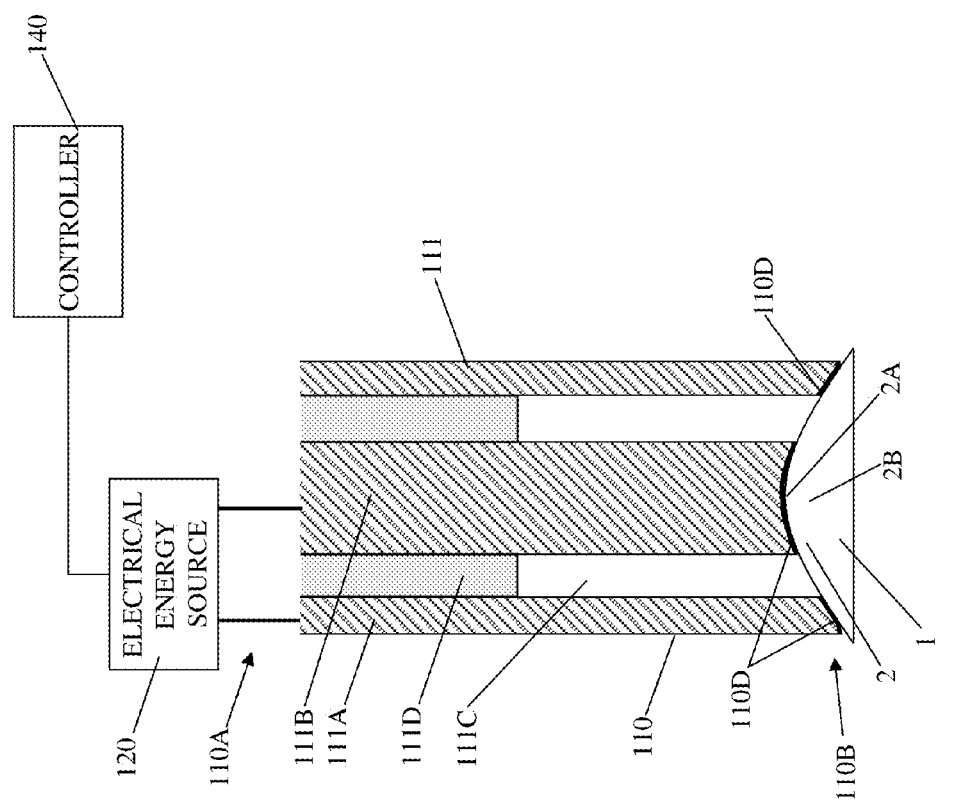
FIG. 1 illustrates an example system for applying heat to a cornea of an eye to cause reshaping of the cornea.

FIG. 1 illustrates an example system for applying energy to a cornea 2 of an eye 1 to generate heat and cause reshaping of the cornea. In particular, FIG. 1 shows an applicator 110 with an electrical energy conducting element 111 that is operably connected to an electrical energy source 120, for example, via conventional conducting cables. The electrical energy conducting element 111 extends from a proximal end 110A to a distal end 110B of the applicator 110. The electrical energy conducting element 111 conducts electrical energy from the source 120 to the distal end 110B to apply energy to the cornea 2, which is positioned at the distal end 110B. In particular, the electrical energy source 120 may include a microwave oscillator for generating microwave energy. For example, the oscillator may operate at a microwave frequency range of 400 MHz to 3000 MHz, and more specifically at a frequency of around 915 MHz or 2450 MHz. As used herein, the term "microwave" may correspond to a frequency range from about 10 MHz to about 10 GHz.

As further illustrated in FIG. 1, the electrical energy conducting element 111 may include two microwave conductors, or electrodes, 111A and 111B, which extend from the proximal end 110A to the distal end 110B of the applicator 110. In particular, the conductor 111A may be a substantially cylindrical outer conductor, while the conductor 111B may be a substantially cylindrical inner conductor that extends through an inner passage extending through the outer conductor 111A. With the inner passage, the conductor 111A may have a substantially tubular shape. The outer conductor 111A and inner conductor 111B may be formed, for example, of aluminum, stainless steel, brass, copper, other metals, coated metals, metal-coated plastic, or any other suitable conductive material.

With the concentric arrangement of conductors 111A and 111B, a substantially annular gap 111C of a selected distance is defined between the conductors 111A and 111B. The annular gap 111C extends from the proximal end 110A to the distal end 110B. A dielectric material 111D may be used in portions of the annular gap 111C to separate the conductors 111A and 111B. The distance of the annular gap 111C between conductors 111A and 111B determines the penetration depth of microwave energy into the cornea 2 according to established microwave field theory. Thus, the microwave conducting element 111 receives, at the proximal end 110A, the electrical energy generated by the electrical energy source 120, and directs microwave energy to the distal end 110B, where the cornea 2 is positioned.

The outer diameter of the inner conductor 111B is preferably larger than the pupil. In general, the outer diameter of the inner conductor 111B may be selected to achieve an appropriate change in corneal shape, i.e., keratometry, induced by the exposure to microwave energy. Meanwhile, the inner diameter of the outer conductor 111A may be selected to achieve a desired gap between the conductors 111A and 111B. For example, the outer diameter of the inner conductor 111B ranges from about 2 mm to about 10 mm while the inner diameter of the outer conductor 111A ranges from about 2.1 mm to about 12 mm. In some systems, the annular gap 111C may be sufficiently small, e.g., in a range of about 0.1 mm to about 2.0 mm, to minimize exposure of the endothelial layer of the cornea (posterior surface) to elevated temperatures during the application of heat by the applicator 110.

A controller 140 may be employed to selectively apply the energy any number of times according to any predetermined or calculated sequence. The controller 140 may include a computer device to control the application of energy according to instructions provided via a computer-readable storage medium. In addition, the controller 140 may include a monitor and keyboard, or other user interface devices for receiving instructions from an operator.

Depending on the instructions, the energy may be applied for any length of time. Furthermore, the magnitude of energy being applied may also be varied. Adjusting such parameters for the application of energy determines the extent of changes that are brought about within the cornea 2. The system attempts to limit the changes in the cornea 2 to an appropriate amount of shrinkage of collagen fibrils in a selected region. When employing microwave energy to generate heat in the cornea 2, for example with the applicator 110, the microwave energy may be applied with low power (of the order of 40 W) and in long pulse lengths (of the order of one second). However, other systems may apply the microwave energy in short pulses. In particular, it may be advantageous to apply the microwave energy with durations that are shorter than the thermal diffusion time in the cornea. For example, the microwave energy may be applied in pulses having a higher power in the range of 500 W to 3 KW and a pulse duration in the range of about 10 milliseconds to about one second.

Referring again to FIG. 1, at least a portion of each of the conductors 111A and 111B may be covered with an electrical insulator to minimize the concentration of electrical current in the area of contact between the corneal surface (epithelium) 2A and the conductors 111A and 111B. In some systems, the conductors 111A and 111B, or at least a portion thereof, may be coated with a material that can function both as an electrical insulator as well as a thermal conductor. A dielectric layer 110D may be employed along the distal end 110B of the applicator 110 to protect the cornea 2 from electrical conduction current that would otherwise flow into the cornea 2 via conductors 111A and 111B. Such current flow may cause unwanted temperature effects in the cornea 2 and interfere with achieving a maximum temperature within the collagen fibrils in a mid-depth region 2B of the cornea 2. Accordingly, the dielectric layer 110D is positioned between the conductors 111A and 111B and the cornea 2. The dielectric layer 110D may be sufficiently thin to minimize interference with microwave emissions and thick enough to prevent superficial deposition of electrical energy by flow of conduction current. For example, the dielectric layer 110D may be a biocompatible material deposited to a thickness of about 51 μm (0.002 inches). In general, an interposing layer, such as the dielectric layer 110D, may be employed between the conductors 111A and 111B and the cornea 2 as long as the interposing layer does not substantially interfere with the strength and penetration of the microwave radiation field in the cornea 2 and does not prevent sufficient penetration of the microwave field and generation of a desired heating pattern in the cornea 2. The dielectric material may be elastic, such as polyurethane and silastic, or nonelastic, such as Teflon® and polyimides. The dielectric material may have a fixed dielectric constant or varying dielectric constant by mixing materials or doping the sheet, the variable dielectric being spatially distributed so that it may affect the microwave hearing pattern in a customized way. The thermal conductivity of the material may have fixed thermal properties (thermal conductivity or specific heat), or may also vary spatially, through mixing of materials or doping, and thus provide a means to alter the heating pattern in a prescribed manner. Another approach for spatially changing the heating pattern is to make the dielectric sheet material of variable thickness. The thicker region will heat less than the thinner region and provides a further means of spatial distribution of microwave heating.

The system of FIG. 1 is provided for illustrative purposes only, and other systems may be employed to apply energy to cause reshaping of the cornea. Other systems are described, for example, in U.S. patent application Ser. No. 12/208,963, filed Sep. 11, 2008, which is a continuation-in-part application of U.S. patent application Ser. No. 11/898,189, filed on Sep. 10, 2007, the contents of these applications being entirely incorporated herein by reference.

As described in U.S. patent application Ser. No. 12/208, 963, a cooling system may be employed in combination with the applicator 110 to apply coolant to the cornea 2 and determine how the energy is applied to the cornea 2. For example, the applicator 110 may include, internally or externally, at least one coolant delivery element in fluid communication with a coolant supply, or reservoir. The coolant delivery element delivers a coolant, or cryogen, from the coolant supply to the distal end of the applicator. In some embodiments, the coolant may be applied more directly to the dielectric layer 110D disposed along the distal end 110B, if the dielectric layer 110D substantially encloses the distal end 110B of the applicator 110. In general, the applicator may be employed to apply coolant to selectively cool the surface 2A of the cornea 2 positioned at the distal end 110B. The delivery of coolant from the coolant delivery element toward the corneal surface 2A, in sequence with the application of heat to the cornea 2, permits the corneal temperature to be increased to cause appropriate shrinkage of the collagen fibers in the targeted mid-depth region 2B and reshape the cornea 2, while also minimizing injury to the outer layer 2A, i.e. the epithelium, of the cornea 2.

In operation, the distal end 110B of the applicator 110 as shown in FIG. 1 is positioned on or near the corneal surface 2A. Preferably, the applicator 110 makes direct contact with the corneal surface 2A. In particular, such direct contact positions the conductors 111A and 111B at the corneal surface 2A, though a thin interposing dielectric layer 110D may be disposed between the conductors 111A and 111B and the corneal surface 2A. Accordingly, direct contact helps ensure that the pattern of microwave heating in the corneal tissue has substantially the same shape and dimension as the gap 111C between the two microwave conductors 111A and 111B.

Prior to positioning of the applicator 110 in contact with the corneal surface 2A, the corneal surface 2A may be scanned to make a topographical map showing the shape and curvature of the surface of the cornea. Then, with the conductors 111A and 111B positioned flush with the corneal surface 2A, the treatment may apply durations of microwave pulses to heat and reshape collagen and coolant pulses to protect the corneal surface. In one aspect, the treatment attempts to shrink the collagen in the cornea 2 and form a precisely controlled annular lesion in approximately the upper 150 μm of the stroma. The microwave treatment raises the temperature of an annulus, just below the surface of the cornea, to a temperature in the range of approximately 60 to 75° C. Using evaporative surface cooling techniques, the system cools the surface of the cornea during treatment to isolate and protect the epithelium and Bowman's membrane from microwave heating. Thus, the treatment is noninvasive, as there is no cutting or penetration of the eye. In one example application, the applicator 110 predictably flattens the central cornea to achieve mild-to-moderate myopic correction (−0.5 to −3.5 diopters, D) without compromising the biomechanical integrity of the cornea.

Accordingly, embodiments according to aspects of the present invention may use microwave energy emitted from the applicator 110, e.g., in a ring-shaped pattern, around the pupil to shrink stromal collagen and modify the dioptric power of the cornea, while a cooling system acts on the corneal surface to minimize thermal damage to the epithelium. In particular, electric field lines form a fringing pattern that extends into the corneal stroma to a depth determined by the applied power and applicator geometry. This electric field causes the polar water molecules to align themselves with the field; the rapid reversal of the sinusoidally-varying field causes frictional heating by these molecules as they rotate in place. This effect does not require a conduction current to flow through a point of electrical contact between a conductor and tissue; heating is caused by a displacement current.

Figure 2A:
FIG. 2A illustrates a high resolution image of a cornea after heat has been applied.
Figure 2B:
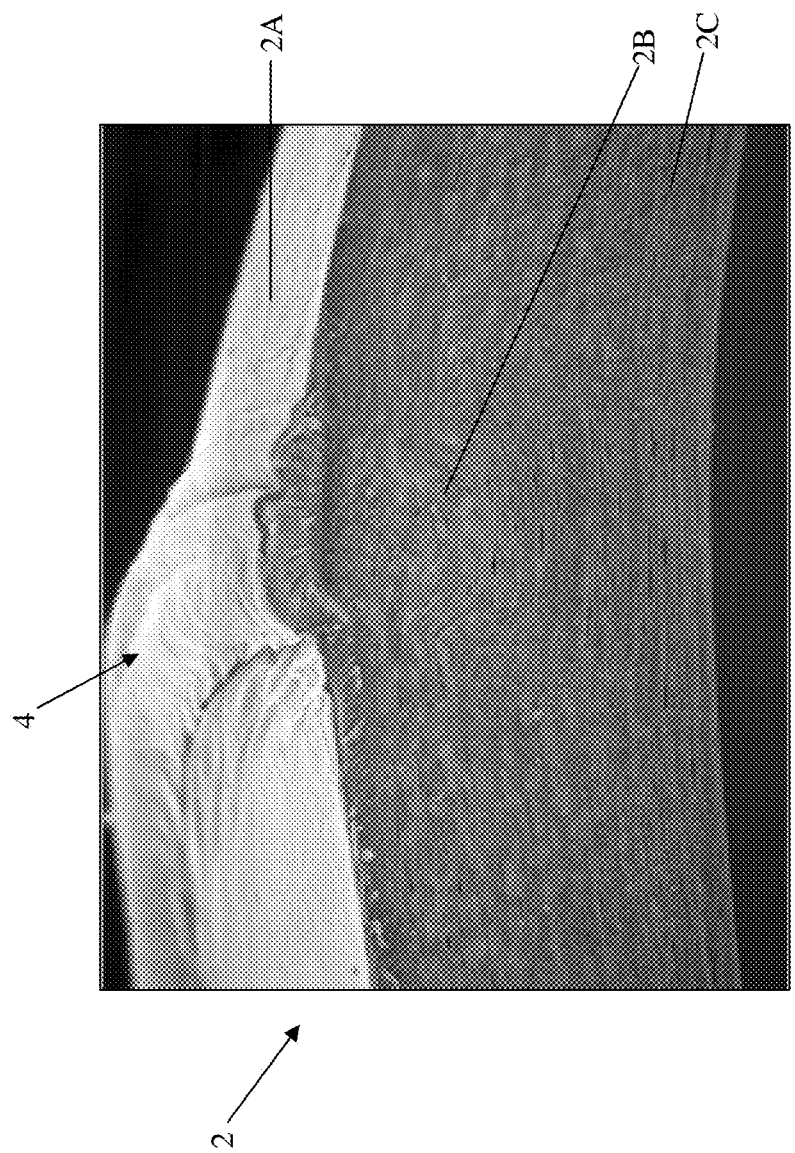
FIG. 2B illustrates another high resolution images of the cornea of FIG. 2A.

FIGS. 2A-D illustrate an example of the effect of applying heat to corneal tissue with a system for applying heat, such as the system illustrated in FIG. 1. In particular, FIGS. 2A and 2B illustrate high resolution images of cornea 2 after heat has been applied. As FIGS. 2A and 2B show, a lesion 4 extends from the corneal surface 2A to a mid-depth region 2B in the corneal stroma 2C. The lesion 4 is the result of changes in corneal structure induced by the application of heat as described above. These changes in structure result in an overall reshaping of the cornea 2. It is noted that the application of heat, however, has not resulted in any heat-related damage to the corneal tissue.

Figure 2C:
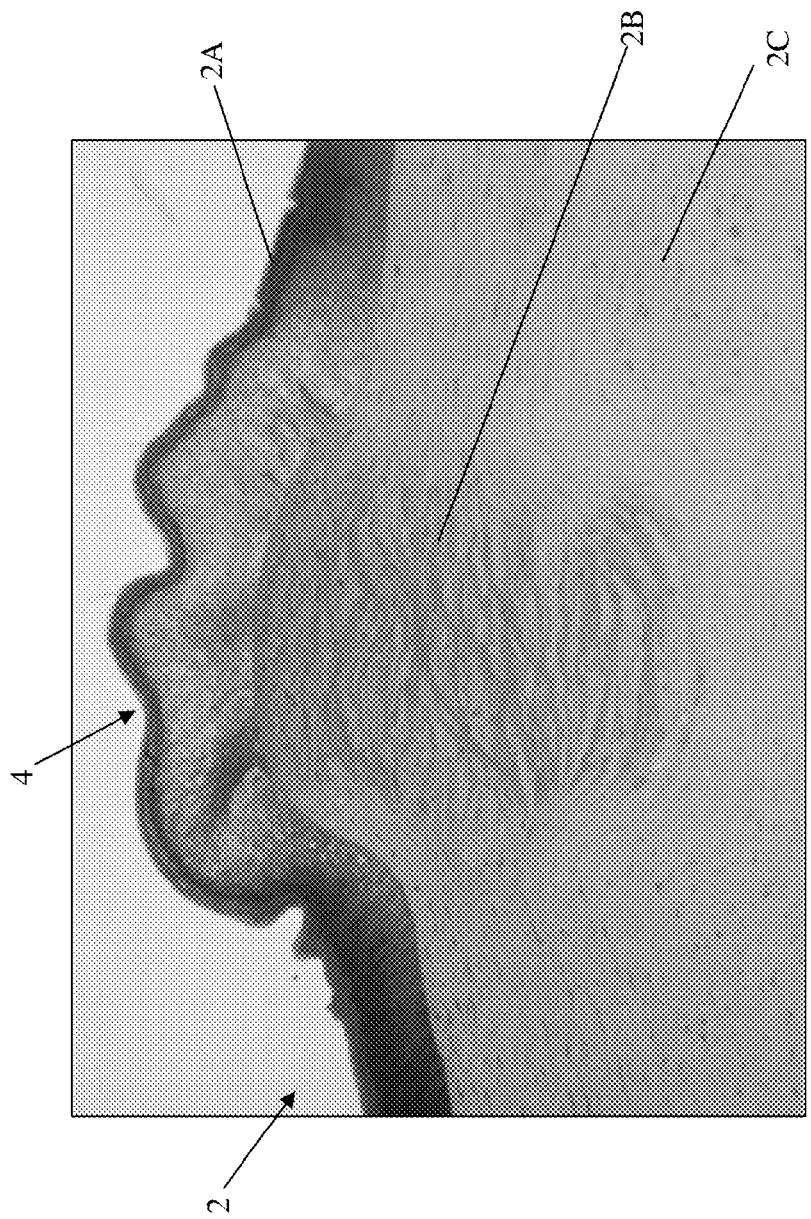
FIG. 2C illustrates a histology image of the cornea of FIG. 2A.
Figure 2D:
FIG. 2D illustrates another histology image of the cornea of FIG. 2A.

As further illustrated in FIGS. 2A and 2B, the changes in corneal structure are localized and limited to an area and a depth specifically determined by an applicator as described above. FIGS. 2C and 2D illustrate histology images in which the tissue shown in FIGS. 2A and 2B has been stained to highlight the structural changes induced by the heat. In particular, the difference between the structure of collagen fibrils in the mid-depth region 2B where heat has penetrated and the structure of collagen fibrils outside the region 2B is clearly visible. Thus, the collagen fibrils outside the region 2B remain generally unaffected by the application of heat, while the collagen fibrils inside the region 2B have been rearranged and formed new bonds to create completely different structures. In other words, unlike processes, such as orthokeratology, which compress areas of the cornea to reshape the cornea via mechanical deformation, the collagen fibrils in the region 2B are in an entirely new state.

In summary, energy is applied to a cornea through an applicator, such as the applicator 110 shown in FIG. 1, to generate heat that produces a desired reshaping of the cornea. Although the heat induces structural changes in the collagen fibrils of the cornea, the desired effects of reshaping the cornea may be mitigated or reversed at least partially if the collagen fibrils continue to change after the desired reshaping has been achieved. Therefore, aspects of the present invention provide approaches for preserving the desired corneal structure and reshaping that result from the application of heat. In particular, embodiments may provide approaches for initiating molecular cross-linking of the corneal collagen to stabilize the corneal tissue and improve its biomechanical strength after the desired shape change has been achieved. For example, cross-linking may be induced in the corneal stroma 2C at the lesion 4 formed by the application of heat as shown in FIGS. 2A-C.

Figure 3A:
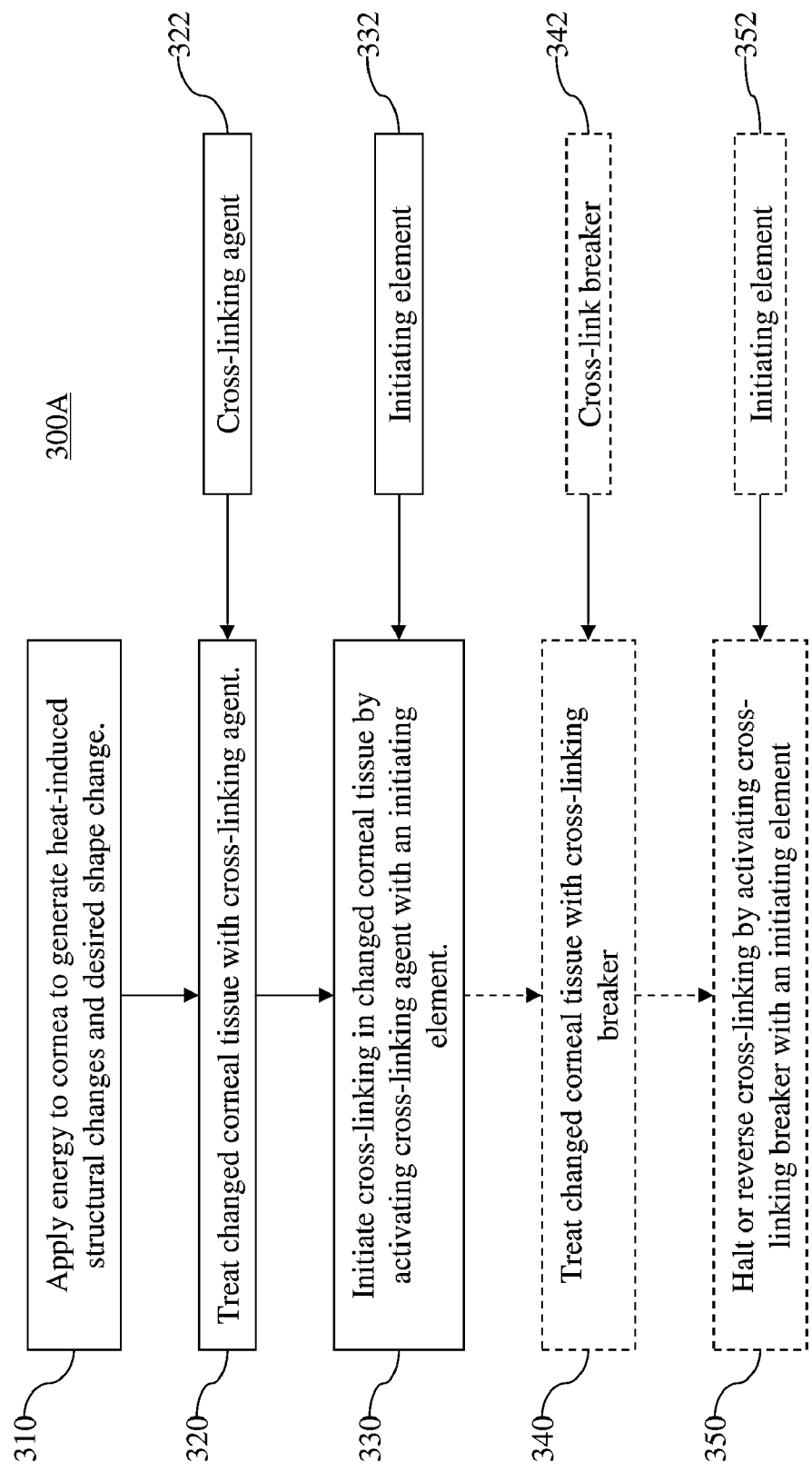
FIG. 3A illustrates an example approach for stabilizing changes in corneal structure induced by the application of energy according to aspects of the present invention.

Referring to FIG. 3A, an example embodiment 300A according to aspects of the present invention is illustrated. Specifically, in step 310, energy is applied to corneal tissue to generate heat-induced structural changes and a desired shape change, as described previously. In step 320, the changed corneal tissue is treated with a cross-linking agent 322. The cross-linking agent may be provided as an ophthalmic preparation that facilitates application to the corneal surface and allows sufficient delivery of the cross-linking agent to the target corneal fibrils below the epithelium. In some embodiments, the cross-linking agent may an ophthalmic solution that is broadly delivered by a dropper, syringe, or the like. Alternatively, the cross-linking agent may be selectively applied as an ophthalmic ointment with an appropriate ointment applicator. The cross-linking agent 322 is then activated in step 330 with an initiating element 332. Activation of the cross-linking agent 322, for example, may be triggered thermally by the application of heat-generating light or microwaves.

According to other aspects of the present invention, glycolaldehyde (GA) may be employed as the cross-linking agent to generate reversible glucose-derived protein cross-links. Advanced glycation endproducts (AGE's) accumulate on most collagenous structures with aging, and the resulting cross-links impart increased rigidity to the tissue. GA is an AGE forming agent and is therefore a physiologically relevant vehicle for mimicking advanced aging and its effects on collagenous structures. Indeed, AGE's produced by GA are similar to those present in normal aging tissues. (See Josephine V. Glenn et al., "AGE-modified substrate induces global gene expression changes in ARPE-19 monolayers: relevance to lysosomal dysfunction and lipofuscin accumulation," Investigative Opthalmology and Visual Science, the contents of which are incorporated herein by reference.)

Figure 3B:
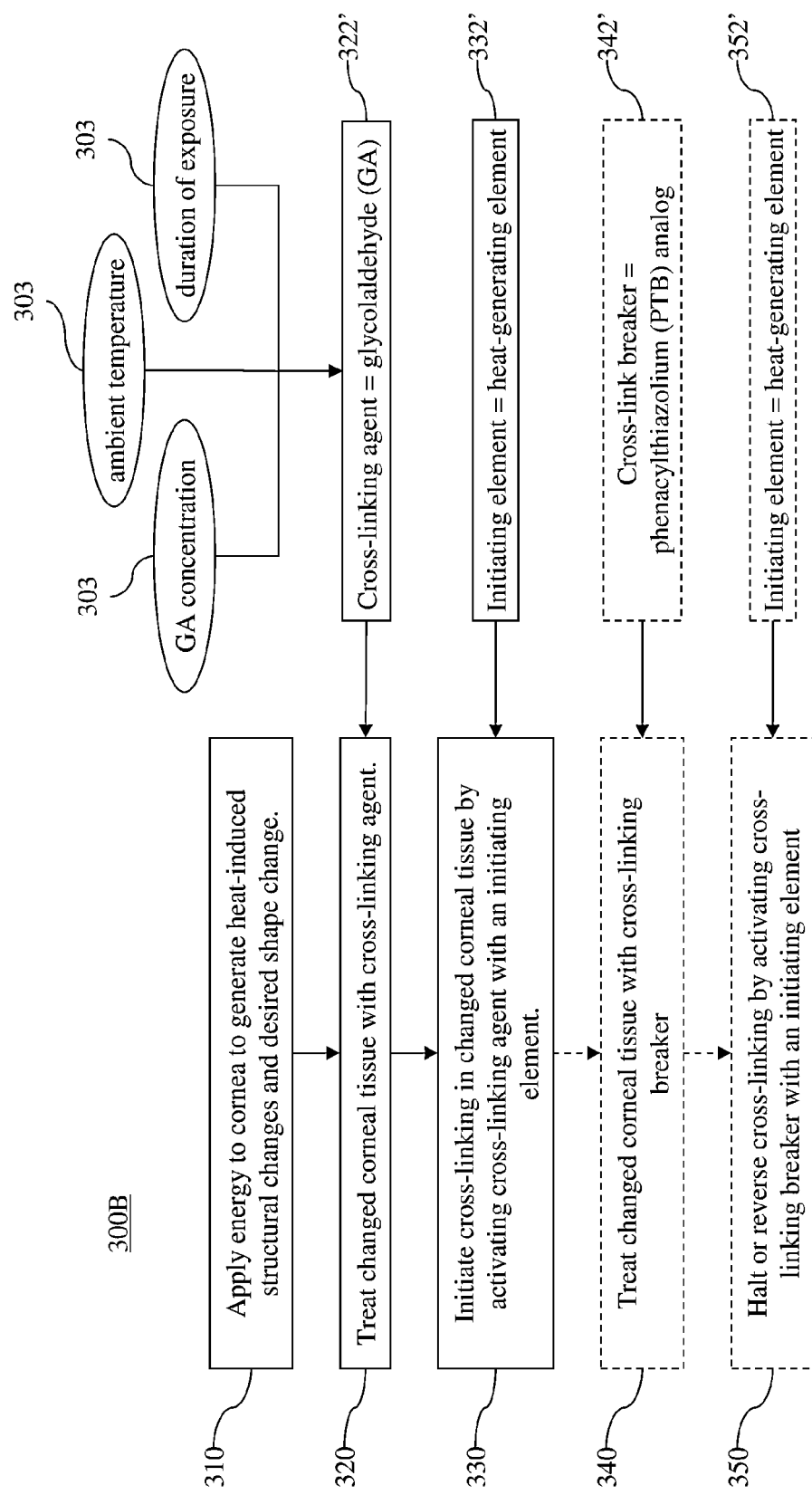
FIG. 3B illustrates another example approach for stabilizing changes in corneal structure induced by the application of energy according to aspects of the present invention.

Thus, as the example embodiment 300B of FIG. 3B shows, GA may be applied topically in step 320 as a cross-linking agent 322' to the changed corneal tissue, i.e., at the site of the lesion 4. In general, cross-linking is only required in the area of the cornea 2 corresponding to the pattern of energy applied. The pattern, for example, may be defined by the shape of the applicator 110 at the distal end 110B, as shown in FIG. 1. The degree of cross-linking, and thus rigidity, may be determined by parameters 303, such as GA concentration, duration of exposure, and ambient temperature, which may be quantified in vitro. A further transient elevation of temperature is selectively applied with a heat-generating element 332' in step 330 to allow topographical localization of exposure for cross-linking via GA 322'. For example, step 330 may apply heat-generating light, such as infrared (IR) lasers, or microwaves to initiate cross-linking in the corneal areas treated with GA 322'.

In further embodiments, the AGE cross-linking created by the GA may be halted or reversed with cross-linking breakers such as the parent compound, phenacylthiazolium bromide (PTB). (See Sara Vasan et al., "An agent cleaving glucose-derived protein crosslinks in vitro and in vivo," Nature, Vol. 382 No. 6588, pp. 275-78 (Jul. 18, 1996), the contents of which are incorporated herein by reference.) Although useful in vitro, PTB may be toxic in vivo. However, analogs of this drug family are available for application in vivo. For example, alagebrium has been licensed for clinical use. Therefore, as shown in FIG. 3B, the cross-linking effects of applying GA may be halted or reversed at least partially by applying a cross-linking breaker 342' to the corneal fibrils in optional step 340. Like the cross-linking agent 322', activity by the cross-linking breaker 342' is initiated in optional step 350 by the applying an initiating element 352', such as a heat-generating element, to the treated areas. Advantageously, the cross-linking breaker provides greater control over the amount and progress of cross-linking that occurs in the corneal fibrils. In some cases, e.g., a corrective procedure, the cross-linking breaker 342' may reverse the effects of cross-linking caused, for example, by the application of the GA 322'. The cross-linking breaker may be provided as an ophthalmic preparation that facilitates application to the corneal surface and allows sufficient delivery of the cross-linking breaker to the target corneal fibrils below the epithelium. In some embodiments, the cross-linking breaker may an ophthalmic solution that is broadly delivered by a dropper, syringe, or the like. Alternatively, the cross-linking breaker may be selectively applied as an ophthalmic ointment with an appropriate ointment applicator. It is understood that the use of the GA 322' and the analog of PTB 342' is described for illustrative purposes only. As more generally shown in steps 340 and 350 of FIG. 3A, embodiments according to aspects of the present invention may employ any agent that halts cross-linking activity, e.g., by a cross-linking agent, and/or reverses the effects of cross-linking activity.

Figure 3C:
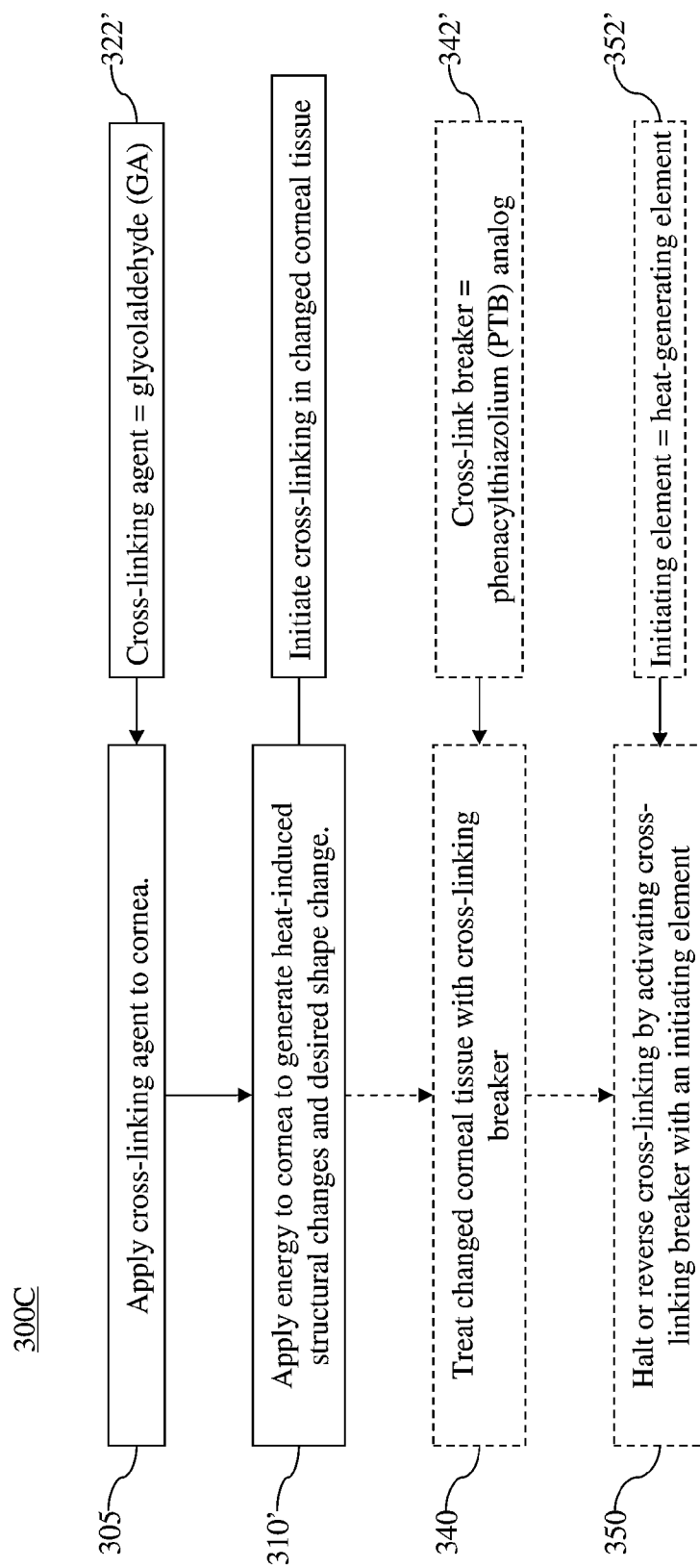
FIG. 3C illustrates yet another example approach for stabilizing changes in corneal structure induced by the application of energy according to aspects of the present invention.

As illustrated in FIG. 3C, an alternative embodiment 300C applies the GA 322' to the cornea 2 in step 305 before energy is delivered to the cornea 2 in step 310. The GA 322' may be applied to areas of desired shape change or may be applied over a broader area. As discussed above, the heat generated by the delivery of energy in step 310 induces a reshaping of the cornea 2. The heat, however, also activates the GA 322' applied previously in step 305. The activation of the GA 322' is localized, because the heat in 310 is applied to selected areas of the cornea 2. For example, after applying the GA 322' to the cornea in step 305, the applicator 110 in FIG. 1 may be employed to deliver energy according to a pattern defined by the distal end 110B of the applicator 110. In particular, the outer electrode 111A and the inner electrode 111B of the energy conducting element 111 define an annular gap 111C. As described previously, the energy in step 310 is delivered in an annular pattern corresponding to this annular gap. Corneal fibrils in the area of this annular pattern experience structural changes. In addition, the GA 322' applied previously to the corneal fibrils in the area of this annular pattern is simultaneously activated. Thus, the embodiment 300C ensures that the GA 322' is activated in the area where the structural changes occur and need be stabilized. Accordingly, in addition to inducing desired shape changes in the cornea 2, the applicator 110 in the embodiment 300C also supplies the heat-generating element 332' which activates the GA 322'. As shown in FIG. 3C, steps 340 and 350 described previously may be optionally executed in alternative embodiment 300C.

As illustrated by the embodiment 300C, cross-linking caused by the GA 322' can be limited to the areas of desired structural change, e.g., the site of the lesion 4. In other words, it is not necessary to apply the GA 322' and the heat-generating element 332' broadly across the entire cornea 2. As described in the previous example, when the applicator 110 in FIG. 1 delivers energy to the cornea 2, the desired structural changes in the cornea 2 occur in the area corresponding to the annular pattern. Therefore, embodiments can limit the activation of the GA 322' to the annular area where the desired structural changes occur. By activating the GA 322' at selected areas of the cornea 2, embodiments can achieve more precise cross-linking activity and minimize the unpredictable refractive changes that may occur with broader activation of the GA 322'.

To activate the GA 322' at desired areas of the cornea, the GA 322' may be applied more precisely to desired areas of the cornea 2 while the heat-generating element 332' may be applied over a broader area. Although the application of the heat-generating element 332' may be broader, the GA 322' primarily affects the cornea 2 in areas where it has been applied. Conversely, the GA 322' may be applied over a broader area and the heat-generating element 332' may be applied more precisely to the desired areas of the cornea 2. Although the application of the GA 322' may be broader in this alternative embodiment, the GA 322' primarily affects the cornea 2 in areas where the heat-generating element 332' has been applied. In further embodiments, however, the GA 322' and the heat-generating element 332' are both applied more precisely to the selected areas of the cornea 2.

Figure 4B:
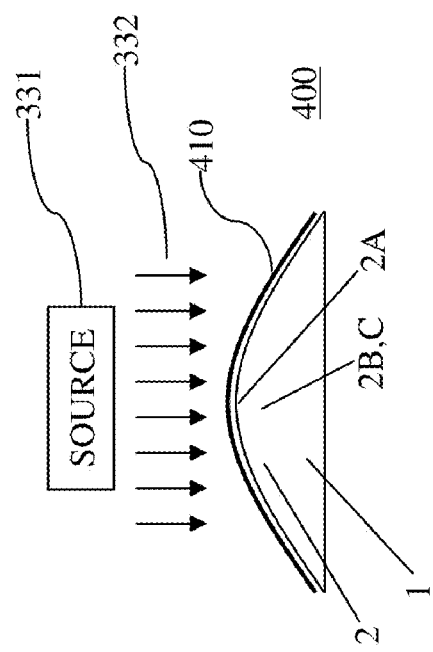
FIG. 4B illustrates an example initiation pattern for the mask of FIG. 4A.

To achieve selective activation of the GA 322', embodiments may apply a mask to ensure that cross-linking activity is limited to desired areas of the cornea 2. As illustrated in the system 400 in FIG. 4A, a mask 410 may be positioned over the corneal surface 2A before the heat-generating element 332', e.g., IR lasers or microwaves, from a source 331 is applied. FIG. 4B illustrates an example pattern 414 for the mask 410. In particular, the mask 410 may be a device similar to a contact lens that is approximately 5 mm in diameter. As described previously, the energy conducting element 111 of the applicator 110 shown in FIG. 1 produces structural changes in the cornea 2 according to an annular pattern. To stabilize these structural changes, cross-linking generally only needs to be initiated along the annular pattern of the structural changes. As a result, the mask 410 of FIG. 4B only allows the heat-generating element 332' from the source 331 to pass to the cornea 2 according to the annular pattern 414. The GA 322' is then activated in areas corresponding to the annular pattern 414. For example, the pattern 414 on the mask 410 may be formed from a material 412 that blocks IR lasers or microwaves. Alternatively or additionally, the material 412 may be an insulating material to prevent unwanted heat transfer to areas outside the pattern 414. In other embodiments, the pattern 414 may be structurally defined as a cut-out from the mask 410. In any case, any initiating element 332' from the source 331 outside this pattern 414 is blocked by the mask 410. Accordingly, the mask 410 provides more precise activation of the GA 322'.

Figure 3D:
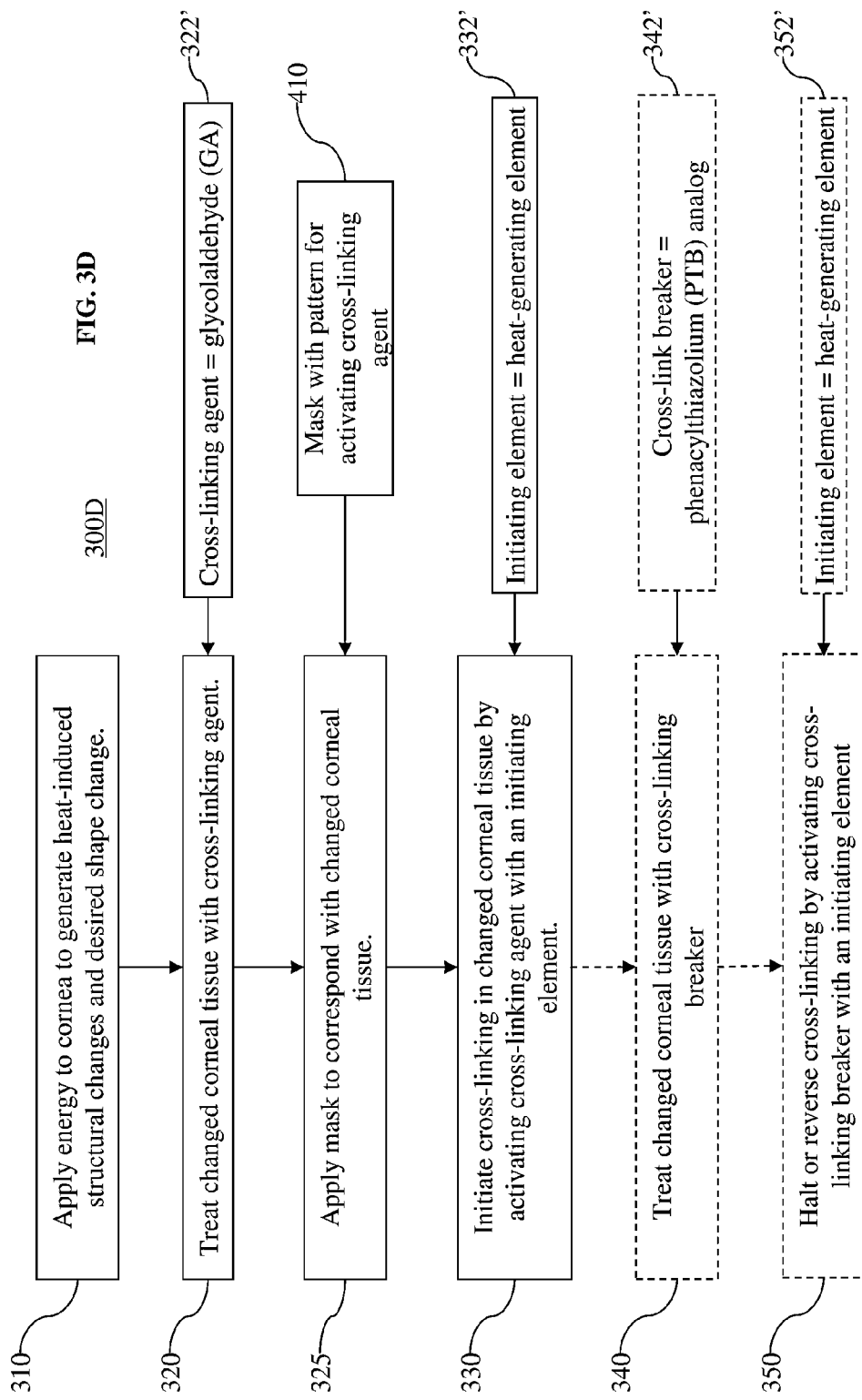
FIG. 3D illustrates a further example approach for stabilizing changes in corneal structure induced by the application of energy according to aspects of the present invention.

Referring to the example embodiment 300D in FIG. 3D, a mask 410 is applied to the eye in step 325 after the GA 322' is applied in step 320. Once the GA 322' has been effectively applied to the stroma, the mask 410 determines more precisely where in the stroma the applied GA 322' should be activated. Thus, in step 330, the heat-generating element 332' is applied to the eye to initiate cross-linking according to a pattern in the mask 410. As shown in FIG. 3D, steps 340 and 350 described previously may be optionally executed in alternative embodiment 300D.

Although the mask 410 is employed to deliver the heat-generating element 332' to the cornea according to a particular pattern, masks may also be employed in some embodiments to deliver the GA 322' and/or the cross-linking breaker 342 according to the specific pattern. Thus, the source 331 of the initiating element shown in FIG. 4A would be replaced by a source of the GA 322'.

Figure 4A:
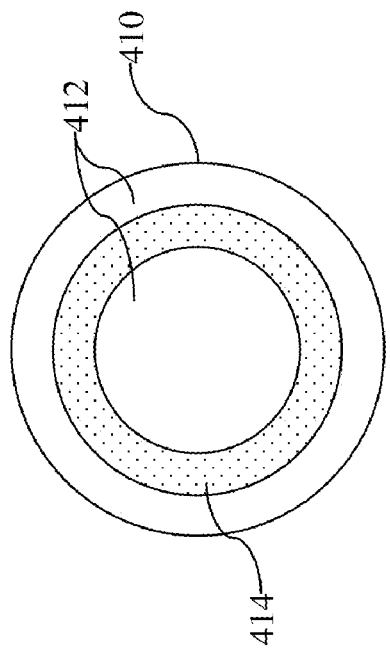
FIG. 4A illustrates an example system that employs a mask to initiate cross-linking in corneal tissue after the application of energy according to aspects of the present invention.
Figures 5A, 5B:
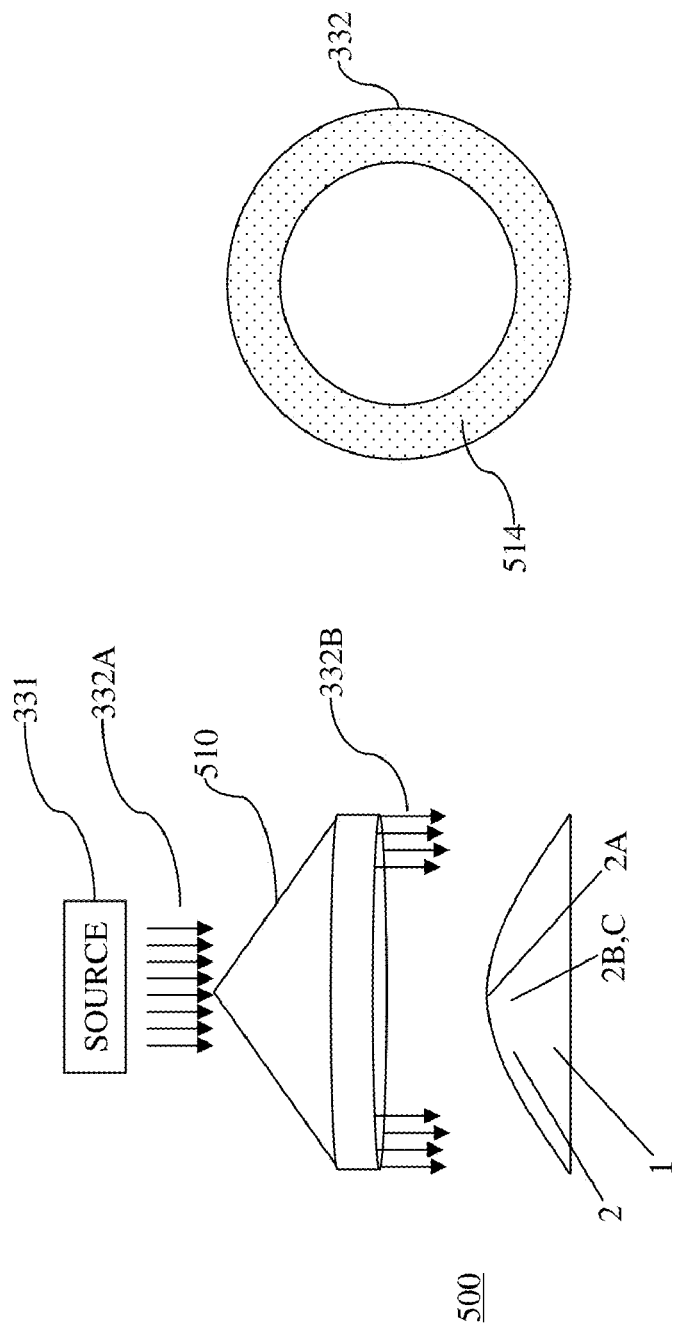
FIG. 5A illustrates an example system that employs an optical device to initiate cross-linking in corneal tissue after the application of energy according to aspects of the present invention.
FIG. 5B illustrates an example initiation pattern corresponding to the optical device of FIG. 5A.

Moreover, although the system 400 may employ a mask 410, the devices employed for patterned initiation of the GA are not limited to the use of such masks. Embodiments include more general systems and methods that activate the GA according to a precise pattern, regardless of the type of device that actually directs the heat-generating element 332' to specific areas of the cornea. For example, as shown in FIG. 5A, a system 500 transforms heat-generating light 332A, e.g., IR lasers, from a source 331 to define a desired pattern 514 as shown in FIG. 5B. In contrast to the system 400, the system 500 does not block the initiating element 332 from a source 331 from reaching areas outside a pattern. As illustrated in FIG. 5A, an optical device, such as an axicon 510, receives the heat-generating light 332A as a collimated beam 332A from the source 331 and transforms the collimated beam 332A into an annulus 332B. The annulus 332B thus delivers the heat-generating light 332A to the cornea 2 according to an annular pattern 514. This annular pattern 514 corresponds to the structural changes that are induced, for example, by the applicator 110 described previously. In other words, the pattern 514 matches the areas where initiation of the GA 322' is desired. In general, any number or types of optical devices, such as lenses, beam-splitters, and the like, may be employed to achieve the desired shape for delivering an initiating element. Moreover, in some embodiments, the use of a mask as illustrated in FIG. 4A may be combined with the use of an optical device.

Although the examples described herein may initiate cross-linking after the application of heat to the cornea 2, e.g., in steps 302 and 312, the technique for initiating cross-linking is not limited to any particular type of eye treatment, such as thermokeratoplasty. Applying a cross-linking agent, such as GA, is generally advantageous for stabilizing the corneal tissue and improving its biomechanical strength, regardless of whether the corneal structure has been changed by treatment.

Moreover, the cross-linking agent may be applied at any time after the treatment. In other words, cross-linking does not have to be necessarily initiated immediately after a treatment. For example, some length of time, e.g., more than one week, may lapse before the cross-linking agent is applied to the cornea after thermokeratoplasty has been employed.

Although the embodiments described herein may initiate cross-linking in the cornea according to an annular pattern defined by an applicator such as the applicator 110 of FIG. 1, the initiation pattern in other embodiments is not limited to a particular shape. Indeed, energy may be applied to the cornea in non-annular patterns, so cross-linking may be initiated in areas of the cornea that correspond to the resulting non-annular changes in corneal structure. Examples of the non-annular shapes by which energy may be applied to the cornea are described in U.S. patent Ser. No. 12/113,672, filed on May 1, 2008, the contents of which are entirely incorporated herein by reference.

While the present invention has been described in connection with a number of exemplary embodiments, and implementations, the present inventions are not so limited, but rather cover various modifications, and equivalent arrangements.

What is claimed is:

1. A method for applying therapy to an eye for stabilizing a pattern of structural changes in corneal fibrils, comprising:
    applying an eye treatment system to corneal fibrils of a cornea of an eye, the eye treatment causing the corneal fibrils to transition from a first structure to a second structure;
    applying an advanced glycation endproduct (AGE) forming agent to the corneal fibrils;
    applying an initiating element to the corneal fibrils and activating the AGE forming agent, the AGE forming agent causing cross-linking in the corneal fibrils to preserve the second structure of the corneal fibrils.

2. The method according to claim 1, wherein the cross-linking agent is glycolaldehyde (GA).

3. The method according to claim 1, wherein applying an initiating element comprises delivering heat-generating light or microwaves to the cornea.

4. The method according to claim 3, wherein delivering heat-generating light to the cornea comprises applying an optical device that directs heat-generating light.

5. The method according to claim 4, wherein the optical device is an axicon that receives the heat-generating light as a collimated beam and transforms the collimated beam into an annulus of light.

6. The method according to claim 1, wherein the eye treatment system includes an energy conducting element that delivers energy according to a selected pattern to the corneal fibrils, the energy causing the transition from the first structure to the second structure, the transition causing a reshaping of the cornea.

7. The method according to claim 6, wherein the energy conducting element comprises an outer conductor and an inner conductor disposed within the outer conductor, the outer conductor and the inner conductor being separated by a gap, a distal end of the energy conducting element defining the selected pattern.

8. The method according to claim 6, wherein applying the initiating element comprises applying energy via the energy conducting element, and the energy from the energy conducting element acting as the initiating element.

9. The method according to claim 1, wherein the eye treatment system causes the transition from the first structure to the second structure according to a selected pattern.

10. The method according to claim 9, wherein applying the AGE forming agent to the cornea comprises applying the AGE forming agent according to the selected pattern.

11. The method according to claim 9, further comprising applying a mask to the cornea, the mask including the selected pattern.

12. The method according to claim 11, wherein applying the AGE forming agent comprises applying the AGE forming agent according to the selected pattern via the mask.

13. The method according to claim 11, wherein applying the initiating element comprises applying the initiating element according to the selected pattern via the mask.

14. A method for changing a pattern of structural changes in corneal fibrils of a cornea of an eye, the structural changes including cross-linking of the corneal fibrils, the method comprising:
applying a cross-linking agent to the corneal fibrils, the cross-linking agent causing cross-linking in the corneal fibrils;
applying a cross-linking breaker to corneal fibrils of a cornea of an eye; and
applying an initiating element to the corneal fibrils and activating the cross-linking breaker, the cross-linking breaker halting or reversing at least partially cross-linking in the corneal fibrils.

15. The method according to claim 14, further comprising applying another initiating element to the corneal fibrils and activating the cross-linking agent.

16. The method according to claim 14, wherein the cross-linking agent is an advanced glycation endproduct (AGE) forming agent.

17. The method according to claim 16, wherein the AGE forming agent is glycolaldehyde (GA).

18. The method according to claim 17, wherein the cross-linking breaker is an analog of phenacylthiazolium bromide (PTB).

19. The method according to claim 18, wherein the cross-linking breaker is alagebrium.

20. The method according to claim 14, further comprising applying an eye treatment system to the eye and causing the corneal fibrils to transition from a first structure to a second structure, the second structure being preserved by the cross-linking.

21. The method according to claim 14, wherein applying the initiating element comprises delivering heat-generating light or microwaves to the cornea.

22. The method according to claim 21, wherein delivering heat-generating light comprises applying an optical device that directs the heat-generating light.

23. The method according to claim 14, further comprising applying a mask to the cornea, the mask including a selected pattern corresponding to the cross-linking in the corneal fibrils.

24. The method according to claim 23, wherein applying the cross-linking breaker comprises applying the cross-linking breaker according to the selected pattern via the mask.

25. The method according to claim 23, wherein applying the initiating element comprises applying the initiating element according to the selected pattern via the mask.

* * * * *